(12) United States Patent
Fujii et al.

(10) Patent No.: US 8,837,871 B2
(45) Date of Patent: Sep. 16, 2014

(54) OPTICAL WAVEGUIDE SENSOR CHIP, OPTICAL WAVEGUIDE SENSOR, AND METHOD FOR MANUFACTURING OPTICAL WAVEGUIDE SENSOR CHIP

(75) Inventors: Mika Fujii, Kanagawa (JP); Mie Matsuo, Kanagawa (JP); Tomohiro Takase, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 338 days.

(21) Appl. No.: 13/176,976

(22) Filed: Jul. 6, 2011

(65) Prior Publication Data
US 2012/0014638 A1 Jan. 19, 2012

(30) Foreign Application Priority Data

Jul. 16, 2010 (JP) ................................. 2010-161638

(51) Int. Cl.
| G02B 6/00 | (2006.01) |
| G02B 6/02 | (2006.01) |
| G01N 21/55 | (2014.01) |
| G01D 5/34 | (2006.01) |
| G02B 6/12 | (2006.01) |

(52) U.S. Cl.
CPC ............ G01D 5/342 (2013.01); G01N 21/552 (2013.01); G02B 2006/12104 (2013.01)
USPC .......................................... 385/12; 427/163.2

(58) Field of Classification Search
USPC .......................................... 385/12; 427/163.2
See application file for complete search history.

(56) References Cited

U.S. PATENT DOCUMENTS

| 5,071,248 A | 12/1991 | Tiefenthaler et al. |
| 5,550,375 A * | 8/1996 | Peters et al. ................... 250/343 |
| 7,679,749 B2 | 3/2010 | Lin et al. |
| 2006/0198762 A1* | 9/2006 | Uematsu et al. ........... 422/82.11 |
| 2007/0081758 A1 | 4/2007 | Tono et al. |
| 2010/0166359 A1 | 7/2010 | Fujimaki et al. |
| 2010/0221408 A1 | 9/2010 | Uematsu et al. |
| 2011/0228276 A1* | 9/2011 | Hiranaka et al. ............... 356/437 |

FOREIGN PATENT DOCUMENTS

| JP | 2004-21220 | 1/2004 |
| JP | 2004-333250 | 11/2004 |
| JP | 2006-47894 | 2/2006 |
| JP | 2006-208359 | 8/2006 |
| JP | 2006-275994 | 10/2006 |
| JP | 2009-85714 | 4/2009 |
| JP | 2010-44290 | 2/2010 |
| WO | WO 2010061536 A1 * | 6/2010 ..................... 356/437 |

* cited by examiner

Primary Examiner — Jerry Blevins
(74) Attorney, Agent, or Firm — Oblon, Spivak, McClelland, Maier & Neustadt, L.L.P.

(57) ABSTRACT

According to one embodiment, an optical waveguide sensor chip includes an optical waveguide layer; a pair of optical elements disposed at both ends of the optical waveguide layer so that light enters the optical waveguide layer and the light exits from the optical waveguide layer; a functional film formed on a predetermined region of the optical waveguide layer; a covering layer formed in a planar region on the light entrance surface of the optical waveguide layer, in which at least the optical elements are disposed; a first through hole configured to allow the light entering the entrance-side optical element to pass therethrough; and a second through hole configured to allow the light exiting from the exit-side optical element to pass therethrough.

18 Claims, 9 Drawing Sheets

OPTICAL WAVEGUIDE SENSOR CHIP, OPTICAL WAVEGUIDE SENSOR, AND METHOD FOR MANUFACTURING OPTICAL WAVEGUIDE SENSOR CHIP

CROSS-REFERENCE TO RELATED APPLICATIONS

This application is based upon and claims the benefit of priority from the prior Japanese Patent Application No. 2010-161638, filed on Jul. 16, 2010; the entire contents of which are incorporated herein by reference.

FIELD

Embodiments described herein relate generally to an optical waveguide sensor chip, an optical waveguide sensor, and a method for manufacturing the optical waveguide sensor chip.

BACKGROUND

As a method of measuring the concentration of a substance included in a sample solution, a method that uses an optical waveguide effect is known. According to an exemplary method, a laser beam enters an optical waveguide layer through an entrance-side grating to thereby generate evanescent waves, and light emitted from an exit-side grating is detected. The power of the evanescent waves changes due to a reaction between substances included in a sample solution and molecules included in a functional film formed on the optical waveguide layer. The concentration of the substance included in the sample solution is measured based on the change in the power of the evanescent waves, which is obtained by detecting the light emitted from the exit-side grating.

A device that measures the concentration of a substance included in a sample solution using such an optical waveguide effect is called an optical waveguide sensor. The optical waveguide sensor includes a transparent substrate formed of glass or quartz, for example, a pair of gratings formed within the substrate on a principal surface of the substrate so as to allow a laser beam to enter and exit, an optical waveguide layer formed of polymer resin having a higher refractive index than the substrate on a principal surface of the substrate including the gratings, and a functional film formed on the optical waveguide layer. In such an optical waveguide sensor, a laser beam enters an optical waveguide from the substrate side through the substrate. Therefore, the substrate needs to be a transparent substrate that transmits the laser beam, and the material to be used as the substrate is limited. Moreover, since the laser beam enters the optical waveguide through the substrate, it is necessary to perform optical design taking the refractive indices of a plurality of materials into account. In addition, the laser beam loses its power when it passes through the substrate.

In the optical waveguide sensor of the related art, since the laser beam enters the optical waveguide through a transparent substrate, there is a problem in that it is necessary to perform optical design taking the refractive indices of a plurality of materials into account, which complicates the optical design. Another problem is that the laser beam loses its power when it passes through the substrate.

DETAILED DESCRIPTION

In general, according to one embodiment, an optical waveguide sensor chip includes an optical waveguide layer, a pair of optical elements which are disposed at both ends of one of boundary surfaces of the optical waveguide layer so as to allow light to enter the optical waveguide layer and exit from the optical waveguide layer, a functional film formed on a predetermined region of the optical waveguide layer, and a covering layer formed on a planar region of a light entrance surface of the optical waveguide layer in which at least the optical elements are disposed. The optical waveguide sensor chip includes a first through hole formed on the covering layer so as to allow the light entering the entrance-side optical element to pass therethrough and a second through hole formed on the covering layer so as to allow the light exiting from the exit-side optical element to pass therethrough.

Exemplary embodiments of an optical waveguide sensor chip, an optical waveguide sensor, and a method for manufacturing the optical waveguide sensor chip will be explained below in detail with reference to the accompanying drawings. The present invention is not limited to the following embodiments.

First Embodiment

Figure 1:
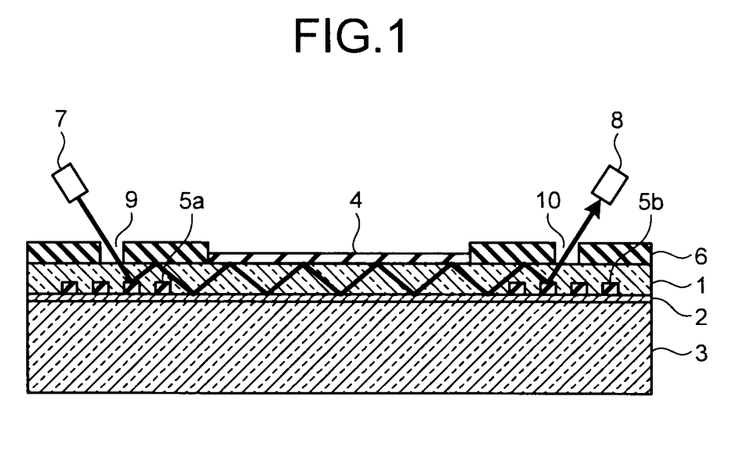
FIG. 1 is a view of one example of an exemplary configuration of an optical waveguide sensor according to a first embodiment.

FIG. 1 is a view showing an exemplary configuration of an optical waveguide sensor according to a first embodiment. The optical waveguide sensor of the present embodiment includes an optical waveguide sensor chip, a light source 7, and a light receiving element 8. Moreover, the optical waveguide sensor chip includes an optical waveguide layer 1, a reflective film 2, a substrate 3, a functional film 4, gratings 5a and 5b, and a protective layer (surface protection layer) 6.

The light source 7 emits light toward the optical waveguide sensor chip so as to enter the optical waveguide layer 1 from the side of the protective layer 6. Moreover, the light receiving element 8 detects light emitted from the side of the protective layer 6 of the optical waveguide sensor chip. A laser diode or the like, for example, can be used as the light source 7. However, the light source 7 is not limited to this, but any light source can be used as long as it can emit single-color light. A photodiode, for example, can be used as the light receiving element 8. However, the light receiving element 8 is not limited to this, and any element can be used.

Figure 2A:
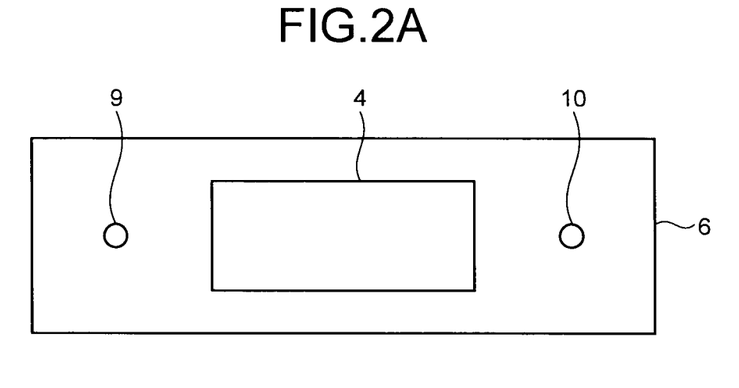
FIGS. 2A and 2B are schematic plan view and cross-sectional view of the optical waveguide sensor chip according to the first embodiment.
Figure 2B:
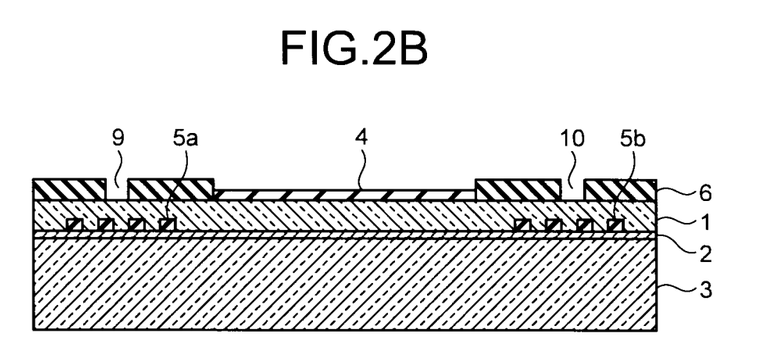

FIGS. 2A and 2B are schematic plan view and cross-sectional view of the optical waveguide sensor chip according to the first embodiment. As shown in FIGS. 2A and 2B, the reflective film 2 is formed between the substrate 3 and the optical waveguide layer 1. Moreover, the grating 5*a* is formed in a region which is disposed on the reflective film 2 (on the opposite side of the surface contacting the substrate 3) at one end in the longitudinal direction of the optical waveguide layer 1 and which includes a region where light from the light source 7 enters. The grating 5*b* is formed in a region which is disposed on the reflective film 2 at the other end and which includes a region where light from the optical waveguide layer 1 exits. The gratings 5*a* and 5*b* are optical elements for allowing light to enter the optical waveguide layer 1 and exit from the optical waveguide layer 1. Other optical elements such as a prism may be used in place of the gratings 5*a* and 5*b*.

The functional film 4 is formed on a predetermined region of the optical waveguide layer 1. The protective layer 6 is formed in a region on the optical waveguide layer 1 other than the region where the functional film 4 is formed. Through holes 9 and 10 are formed in the protective layer 6.

The substrate 3 functions as a rear surface protective layer which is in contact with the optical waveguide layer 1 on a surface (rear surface) where the functional film 4 is not formed and which protects the optical waveguide layer 1 from mechanical damage or the like applied from the rear surface.

The through hole 9 is formed so as to allow the light emitted from the light source 7 to enter the optical waveguide layer 1 without being blocked by the protective layer 6. Moreover, the through hole 9 is formed so that its planar position (position within a surface perpendicular to the thickness direction of the optical waveguide sensor chip) is within the planar position where the entrance-side grating 5*a* is formed. The through hole 10 is formed so as to allow the light exiting from the optical waveguide layer 1 to enter the light receiving element 8 without being blocked by the protective layer 6. Moreover, the through hole 10 is formed so that its planar position is within the planar position where the exit-side grating 5*b* is formed.

FIGS. 2A and 2B are views schematically showing the configuration and the respective constituent elements are not drawn to actual scale. In this example, that the optical waveguide sensor chip is assumed to be about 16 mm in the longitudinal direction and about 6.5 mm in the lateral direction. Moreover, the substrate 3, the optical waveguide layer 1, and the protective layer 6 are assumed to be as thick as about 700 µm, about 30 µm, and about 3 µm, respectively. The functional film 4 is assumed to be about 7 mm and about 4 mm in the longitudinal and lateral directions of the optical waveguide sensor chip, respectively. The respective regions of the gratings 5*a* and 5*b* are assumed to be 2 to 3 mm and about 4.5 mm in the longitudinal and lateral directions of the optical waveguide sensor chip, respectively. These sizes are exemplary, and the respective constituent elements are not limited to these sizes.

Although the sizes of the through holes 9 and 10 depend on the size of the light beam emitted from the light source 7, the diameter thereof is set to about 1 to 5 mm, for example. Although the through holes 9 and 10 have a cylindrical shape in FIGS. 2A and 2B, the shape is not limited to this, but other shapes such as a quadratic prism shape or a tapered shape may be used.

In the optical waveguide sensor of the present embodiment, light emitted from the light source 7 enters the optical waveguide layer 1 through the through hole 9 and the entrance-side grating 5*a*, whereby evanescent waves are generated. Moreover, the change in the power of the evanescent waves due to a reaction between a sample solution or the like introduced on the functional film 4 and molecules or the like included in the functional film 4 formed on the optical waveguide layer 1 is detected by the light receiving element 8 detecting the light emitted through the exit-side grating 5*b* and the through hole 10. The amount of change in the light detected by the light receiving element 8 depends on the concentration of a detection target substance included in the sample solution or the like (that is, a substance that reacts with the molecules or the like included in the functional film 4). Thus, by calculating the amount of change in the light detected by the light receiving element 8, it is possible to detect the concentration of the detection target substance included in the sample solution or the like.

In the optical waveguide sensor of the related art, for example, an optical waveguide layer is formed on a substrate, light enters the optical waveguide layer, and light emitted toward the substrate side from the optical waveguide layer is detected. Therefore, the substrate needs to be formed of a material capable of transmitting the light entering the optical waveguide layer. Moreover, in this case, there is a problem in that two boundary phenomena occur; that is, the boundary between air and the substrate and the boundary between the substrate and the optical waveguide layer. When a transparent material is used for the substrate, and light enters the optical waveguide layer through the substrate, there is a problem in that it is necessary to perform optical design taking the refractive indices of a plurality of materials into account, which complicates the optical design. Another problem is that the light loses its power when it passes through the substrate.

A case where light enters from the side of a protective layer formed on the optical waveguide layer may be considered. However, in this case, similarly to the case of using a transparent substrate, there is a problem in that it is necessary to perform optical design taking the refractive indices of a plurality of materials into account, which complicates the optical design. Another problem is that the light loses its power when it passes through the substrate.

In contrast, according to the optical waveguide sensor of the present embodiment, the light from the light source 7 enters the optical waveguide layer 1 through the through hole 9 formed in the protective layer 6, and the light exits from the optical waveguide layer 1 through the through hole 10. Therefore, it is not necessary to form the substrate 3 or the protective layer 6 using a transparent material. For example, when a silicon substrate is used as the substrate 3, the manufacturing technique of semiconductor chips can be applied to manufacturing of the optical waveguide sensor chip. Moreover, since it is possible to allow the light from the light source 7 to directly enter the optical waveguide layer 1, it is not necessary to perform optical design taking the refractive indices of a plurality of materials into account. Moreover, the light does not lose its power.

Furthermore, since the optical waveguide sensor of the present embodiment includes the reflective film 2, it is possible to eliminate optical limitations on the substrate 3 and to broaden the choice of possible materials of the substrate 3. Although the reflective film 2 is provided in the present embodiment, the reflective film 2 may be omitted by forming the substrate 3 using a material such as metal and performing processing so as to have a mirror-finished surface. In this case, the choice of possible materials of the substrate 3 becomes narrower than the case of having the reflective film 2. However, by allowing the light from the light source 7 to enter the optical waveguide layer 1 through the through hole 9 and exit through the through hole 10, it is possible to obtain an advantageous effect that it is not necessary to perform optical design taking the refractive indices of a plurality of materials into account, and the light does not lose its power.

Although any material that is generally used as an optical waveguide may be used as the optical waveguide layer 1, glass, an organic film, and the like, for example, can be used.

Although any material having a high mirror reflectance may be used as the reflective film 2, a mirror-finished metal thin film of aluminum or silver or a reflective resin film can be used, for example.

As the protective layer 6, a material which has a lower refractive index than the optical waveguide layer 1 and which does not react with the sample solution or the like is used. The protective layer 6 prevents the sample solution from contacting the optical waveguide layer 1 in regions other than the region where the functional film 4 is formed and also prevents the functional film 4 from being formed in regions other than a predetermined region during the manufacturing process of the optical waveguide sensor chip. Although the protective layer 6 may be formed by any method, a method, for example, in which the optical waveguide layer 1 is formed on the substrate 3, and a pattern is transferred to a portion of the optical waveguide layer 1, excluding the region where the functional film 4 and the through holes 9 and 10 are formed using a printing method, an imprint method, or the like is ideally used. A material having excellent water-repellent properties is preferably used as the material of the protective layer 6, and for example, a fluoride resin or the like can be used.

When the reflective film 2 is used, any material can be used as the substrate 3 since no special optical properties such as transparency are required. For example, the use of a silicon substrate gives an advantageous effect that the manufacturing process of semiconductor chips. Although glass may be used if heat resistance is required, in the present embodiment, glass having a low transparency (low grade) or the like can be used since transparency is not required. Moreover, plastics or the like may be used.

Any material of which the refractive index shows a significant difference from the optical waveguide layer 1 may be used as the gratings 5a and 5b, and titanium dioxide can be used, for example.

The functional film 4 includes a film body which is made up of a film-forming polymer compound and the like, and in which an enzyme, a pigment, or the like that reacts with the detection target substrate of the optical waveguide sensor of the present embodiment is maintained. For example, if the detection target substance is glucose, the functional film 4 is made up of an oxidative enzyme or a reductive enzyme of glucose, a color-producing reagent, a reagent that reacts with a product of the enzyme to generate a substance which colors the color-producing reagent, and a film-forming polymer compound. Moreover, the functional film 4 includes a permeability promotor as necessary. When glucose oxidase is used as the oxidative enzyme of glucose, for example, peroxidase can be used as the reagent that generates a substrate which colors the color-producing reagent, and 3,3',5,5'-tetramethyl benzyne or the like can be used as the color-producing reagent. Moreover, a cellulose polymer compound can be used as the film-forming polymer compound, for example.

Next, a method for manufacturing the optical waveguide sensor chip according to the present embodiment will be described. The manufacturing method described below is an example of the method for manufacturing the optical waveguide sensor chip according to the present embodiment, and the method for manufacturing the optical waveguide sensor chip according to the present embodiment is not limited to this.

FIGS. 3A to 3G are views showing an example of the method for manufacturing the optical waveguide sensor chip according to the present embodiment. In this example, a case in which the substrate 3 is a silicon substrate, the optical waveguide layer 1 and the protective layer 6 are organic thin films, and the reflective film 2 is a metal thin film will be described as an example.

Figure 3A:
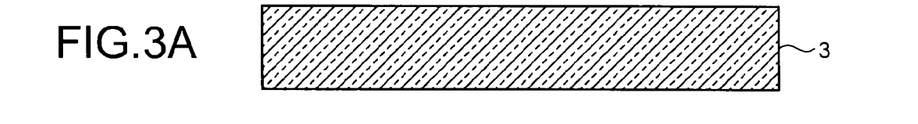
FIGS. 3A to 3G are views of one example of a method for manufacturing the optical waveguide sensor chip according to the first embodiment.
Figure 3B:
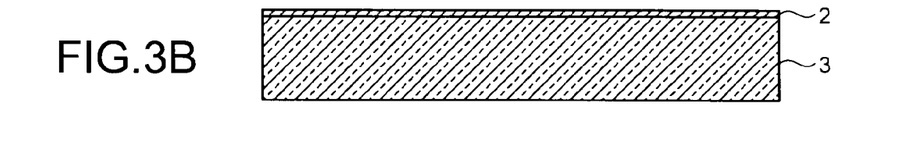

First, a substrate 3 is prepared as shown in FIG. 3A, and a reflective film 2 which is a metal thin film is formed on a surface of the substrate 3 as shown in FIG. 3B. As a method for forming a metal thin film, plating, sputtering, chemical vapor deposition (CVD), and the like can be used. Then, the metal thin film is polished and mirror-finished to obtain the reflective film 2.

Figure 3C:
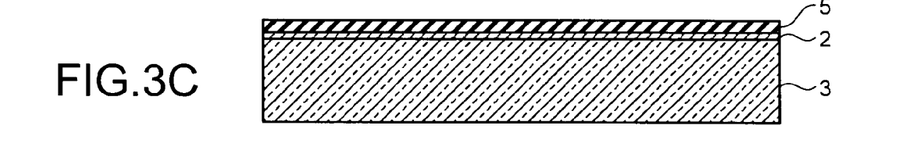
Figure 3D:
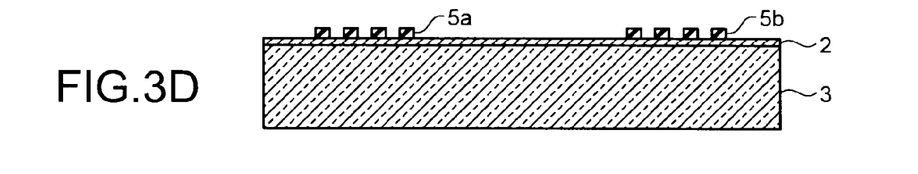

Subsequently, as shown in FIG. 3C, a thin film 5 of a grating material is formed on the reflective film 2 by sputtering, CVD, or the like. After that, as shown in FIG. 3D, the thin film 5 is etched in accordance with a resist pattern to form a pattern, whereby gratings 5a and 5b are formed at two locations of the entrance side and the exit side. Although the thin film 5 may be etched by any method, reactive ion etching (RIE) can be used, for example.

Figure 3E:
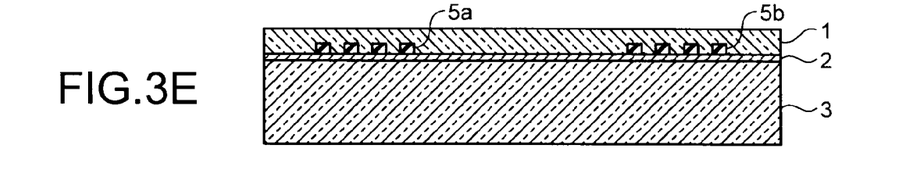

Subsequently, as shown in FIG. 3E, an optical waveguide layer 1 is formed on the reflective film 2 and the gratings 5a and 5b. For example, the optical waveguide layer 1 can be formed by applying a liquid material of the optical waveguide layer 1 by spin coating and then curing the liquid material. Any material having a higher refractive index than the protective layer 6 may be used as the material of the optical waveguide layer 1, and a thermoplastic resin and a thermosetting resin may be used.

Figure 3F:
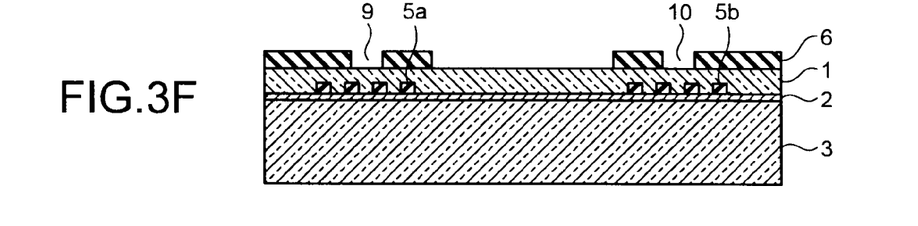

Subsequently, as shown in FIG. 3F, a protective layer 6 is formed on the optical waveguide layer 1. In this case, the protective layer 6 is formed in a region of the optical waveguide layer 1, excluding a predetermined region where the functional film 4 is formed and the through holes 9 and 10 by a printing method, an imprint method, or the like.

Figure 3G:
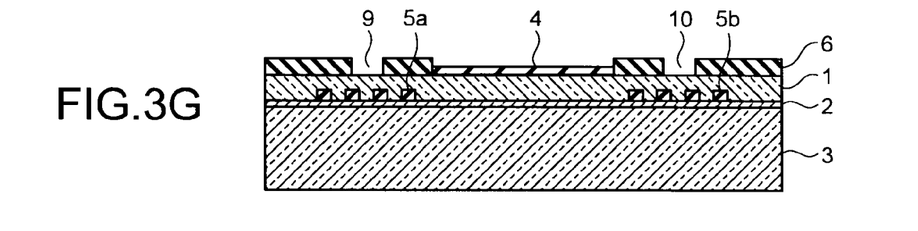

Subsequently, as shown in FIG. 3G, a functional film 4 is formed in a predetermined region (a region of the optical waveguide layer 1 where the protective layer 6 is not formed, excluding the through holes 9 and 10). As a method for forming the functional film 4, a method of dispersing a film-forming polymer compound containing a reagent such as an enzyme or a pigment in a solvent, dispensing the solution to an opening, and then, volatilizing the solvent can be used, for example.

In the present embodiment, an example in which one light source 7 and one light receiving element 8 are provided has been described. However, when two light sources 7 and two light receiving elements 8 are provided, two entrance-side through holes and two exit-side through holes may be provided. For example, when two light sources 7 are provided and the two entrance positions are close to each other, two light beams may pass through one through hole and may pass through the respective through holes. The same is applied to the exit-side through holes.

In the above example, although a case in which an organic material is used as the material of the optical waveguide layer 1 has been described, a silicon oxide or the like may be used for the optical waveguide layer 1. When a silicon oxide is used for the optical waveguide layer 1, a silicon oxide film may be formed on the reflective film 2.

Moreover, although in the present embodiment, the protective layer 6 is made up of one layer, the protective layer 6 may be made up of multiple layers. In this case, the through holes 9 and 10 are provided so as to penetrate through all of these multiple layers. Moreover, the constituent layers other than the protective layer 6 may be formed above or below (between the optical waveguide layer 1 and the protective layer 6). In this case, all layers starting from the upper surface (the light entrance side) of the optical waveguide sensor chip and reaching the surface of the optical waveguide layer 1 may be regarded as one covering layer, and the through holes 9 and 10 may be provided so as to penetrate through the covering layer so that light entering the optical waveguide layer 1 passes through the through holes 9 and 10. In other words, when a covering layer formed in a region including a planar region where at least the gratings 5a and 5b are formed is present between the light entrance surface (the light exiting surface) of the optical waveguide layer 1 and the surface of the optical waveguide sensor chip (the surface on the light entrance side), the through holes 9 and 10 may be formed in the covering layer so that light entering the optical waveguide layer 1 (the grating 5a) or light exiting from the optical waveguide layer 1 passes through the through holes 9 and 10.

As described above, in the present embodiment, the thermoelastic stresses 9 and 10 are formed on the protective layer 6, the light from the light source 7 enters the optical waveguide layer 1 through the through hole 9, and the light exiting from the optical waveguide layer 1 enters the light receiving element 8 through the through hole 10. Therefore, it is possible to broaden the choice of possible materials of the substrate 3. Moreover, it is not necessary to perform optical design taking the refractive indices of a plurality of materials into account, and light does not lose its power. Furthermore, when a silicon substrate is used as the substrate 3, since a semiconductor manufacturing process can be used in many process steps, it is possible to manufacture an optical waveguide sensor chip with high accuracy and productivity. Furthermore, when the reflective film 2 is provided, it is possible to further broaden the choice of possible materials of the substrate 3. In addition, the substrate 3 functions as a light blocking film depending on the material of the substrate 3.

Second Embodiment

Figure 4:
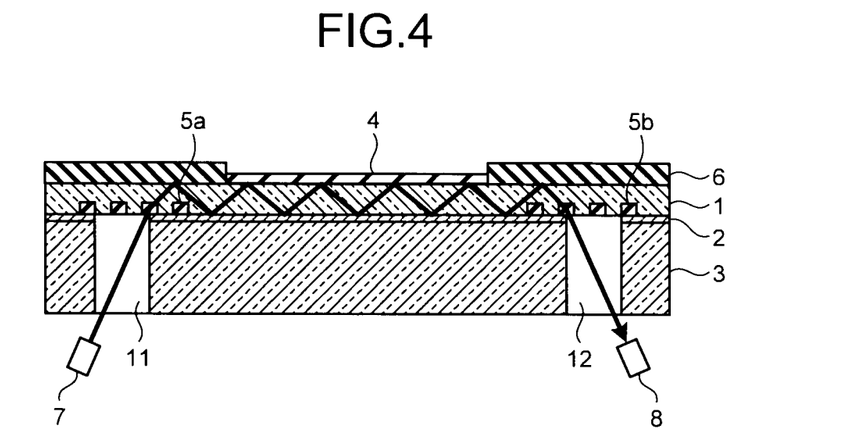
FIG. 4 is a view of one exemplary configuration of an optical waveguide sensor according to a second embodiment.

FIG. 4 is a view showing an exemplary configuration of an optical waveguide sensor according to a second embodiment. The optical waveguide sensor of the present embodiment includes an optical waveguide sensor chip, a light source 7, and a light receiving element 8. The optical waveguide sensor chip of the present embodiment includes an optical waveguide layer 1, a reflective film 2, a substrate 3, a functional film 4, gratings 5a and 5b, and a protective layer 6 similarly to the first embodiment. However, unlike the first embodiment, the through holes 9 and 10 are not formed in the protective layer 6, but through holes 11 and 12 are formed on the reflective film 2 and substrate 3. Moreover, in the present embodiment, light emitted from the light source 7 enters the optical waveguide layer 1 through the through hole 11, and light exiting from the optical waveguide layer 1 enters the light receiving element 8 through the through hole 12. Constituent elements having the same functions as those of the first embodiment will be denoted by the same reference numerals as the first embodiment, and redundant description thereof will not be repeated. The difference from the first embodiment will be described below.

Although the through holes 9 and 10 were formed in the protective layer 6 in the first embodiment, the through holes 11 and 12 are formed in the substrate 3 and the reflective film 2. Moreover, the light emitted from the light source 7 enters the optical waveguide layer 1 from the side of the substrate 3 through the through hole 11, and the light exiting from the optical waveguide layer 1 exits from the side of the substrate 3 through the through hole 12. Therefore, the functional film 4 and the through holes 11 and 12 are not disposed in the same surface but are disposed on the opposite side of the optical waveguide sensor chip. Accordingly, it is possible to prevent contamination of the optical waveguide layer 1 due to entrance of a sample through the through holes 11 and 12 when the sample is introduced to the functional film 4.

The through hole 11 is formed so as to allow the light emitted from the light source 7 to enter the optical waveguide layer 1 without being blocked by the substrate 3 and the reflective film 2. Moreover, the through hole 11 is formed so that its planar position (position within a surface perpendicular to the thickness direction of the optical waveguide sensor chip) is within the planar position where the entrance-side grating 5a is formed. The through hole 12 is formed so as to allow the light exiting from the optical waveguide layer 1 to enter the light receiving element 8 without being blocked by the substrate 3 and the reflective film 2. Moreover, the through hole 12 is formed so that its planar position is within the planar position where the exit-side grating 5b is formed.

Although the sizes of the through holes 11 and 12 depend on the size of the light beam emitted from the light source 7, the diameter thereof is set to about 1 to 2 mm, for example. Although the through holes 9 and 10 have a cylindrical shape in FIGS. 2A and 2B, the shape is not limited to this, but other shapes such as a quadratic prism shape or a tapered shape may be used.

The configuration and function of the optical waveguide sensor of the present embodiment and the materials of the respective constituent elements are the same as those of the optical waveguide sensor of the first embodiment, except that the through holes are formed at a different position, and the entrance and exiting directions are different. However, since the through holes 11 and 12 are formed in the substrate 3, it is preferable to make the substrate 3 thinner than that of the first embodiment (for example, about 100 to 300 μm).

Next, a method for manufacturing the optical waveguide sensor chip according to the present embodiment will be described. The manufacturing method described below is an example of the method for manufacturing the optical waveguide sensor chip according to the present embodiment, and the method for manufacturing the optical waveguide sensor chip according to the present embodiment is not limited to this.

FIGS. 5A to 5G are views showing an example of the method for manufacturing the optical waveguide sensor chip according to the present embodiment. In this example, a case in which the substrate 3 is a silicon substrate, the optical waveguide layer 1 and the protective layer 6 are organic thin films, and the reflective film 2 is a metal thin film will be described as an example.

Figure 5A:
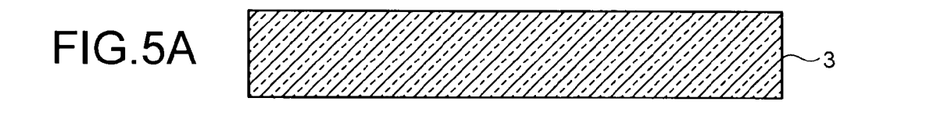
FIGS. 5A to 5G are views of one example of a method for manufacturing the optical waveguide sensor chip according to the second embodiment.
Figure 5B:
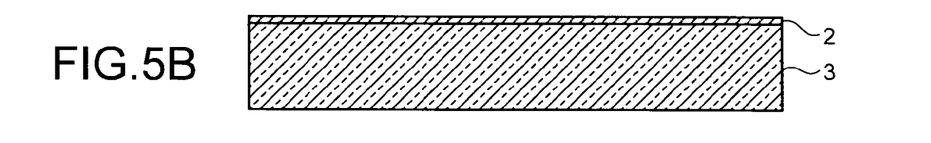
Figure 5C:
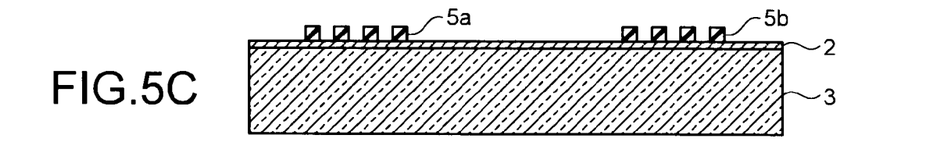
Figure 5D:
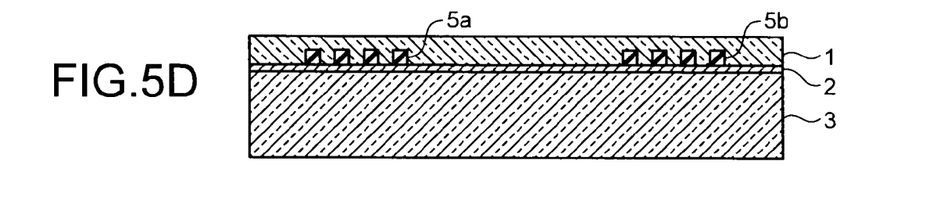
Figure 5E:
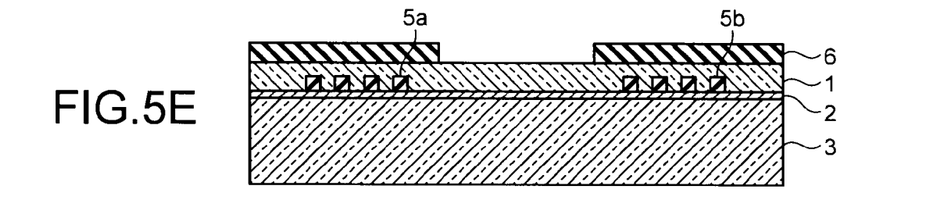

The steps shown in FIGS. 5A to 5D (up to the step of forming the optical waveguide layer 1) are the same as those of the first embodiment, and description thereof will not be repeated. After forming the optical waveguide layer 1, a protective layer 6 is formed on the optical waveguide layer 1 as shown in FIG. 5E. In this case, the protective layer 6 is formed in a region of the optical waveguide layer 1, excluding a predetermined region where the functional film 4 is formed by a printing method, an imprint method, or the like.

Figure 5F:
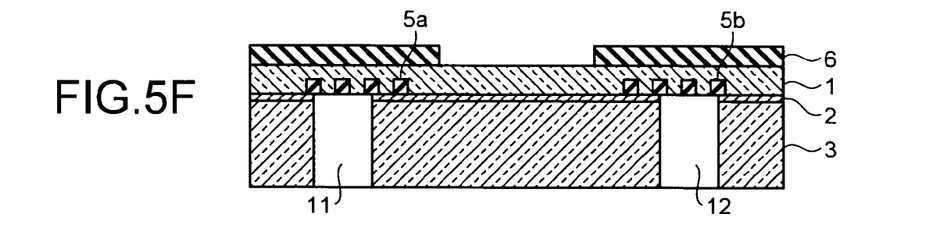

Subsequently, as shown in FIG. 5F, through holes 11 and 12 are formed in the substrate 3 and the reflective film 2. Although the through holes 11 and 12 may be formed by any method, processing accuracy can be improved by performing patterning using a resist and performing wet-etching or RIE.

Figure 5G:
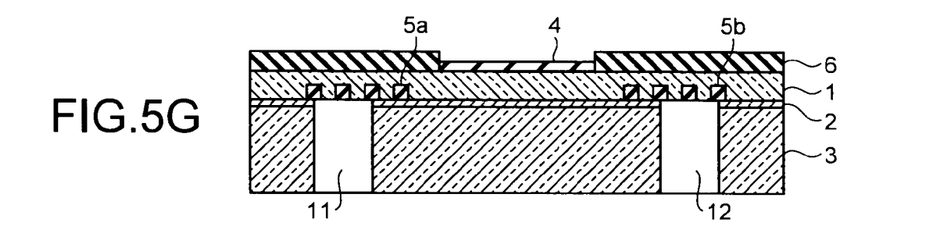

Subsequently, as shown in FIG. 5G, a functional film 4 is formed on a predetermined region. As a method for forming the functional film 4, a method of dispersing a film-forming polymer compound containing a reagent such as an enzyme or a pigment in a solvent, dispensing the solution to an opening, and then, volatilizing the solvent can be used, for example.

Similarly to the first embodiment, by forming the substrate 3 using metal or the like, the reflective film 2 may be omitted. Moreover, the through holes 11 and 12 may be buried by a member formed of a transparent material.

Moreover, in the present embodiment, the through holes 11 and 12 are provided so as to penetrate through the substrate 3 and the reflective film 2. In other words, this corresponds to the case described in the first embodiment in which the substrate 3 and the reflective film 2 are formed as the covering layer which is formed between the light entrance surface (the light exiting surface) of the optical waveguide layer 1 and the surface of the optical waveguide sensor chip (the surface on the light entrance side) in a region including a planar region where at least the gratings 5a and 5b are formed.

In the first and present embodiments, although a case in which the light entrance surface of the optical waveguide layer 1 and the light exiting surface of the optical waveguide layer 1 are the same, the entrance surface and the exiting surface may be different from each other. In this case, the through holes are formed in the covering layer on the corresponding surfaces. For example, when light enters from the side of the protective layer 6 and exits from the side of the substrate 3, the through hole 9 may be formed in the protective layer 6 similarly to the first embodiment, and the through hole 12 may be formed in the substrate 3 and the reflective film 2.

As described above, in the present embodiment, the thermoelastic stresses 11 and 12 are formed on the substrate 3 and the reflective film 2, the light from the light source 7 enters the optical waveguide layer 1 through the through hole 11, and the light exiting from the optical waveguide layer 1 enters the light receiving element 8 through the through hole 12. Therefore, it is possible to obtain the same advantageous effects as the first embodiment and to prevent contamination of the optical waveguide layer 1 when introducing a sample to the functional film 4.

Third Embodiment

Figure 6:
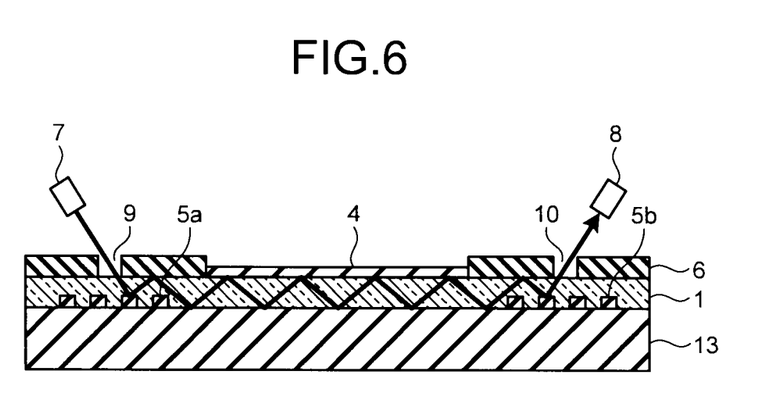
FIG. 6 is a view of an exemplary configuration of an optical waveguide sensor according to a third embodiment.

FIG. 6 is a view showing an exemplary configuration of an optical waveguide sensor according to a third embodiment. The optical waveguide sensor of the present embodiment includes an optical waveguide sensor chip, a light source 7, and a light receiving element 8. The optical waveguide sensor chip of the present embodiment includes an optical waveguide layer 1, a substrate 13, a functional film 4, gratings 5a and 5b, and a protective layer 6. Moreover, through holes 9 and 10 are formed in the protective layer 6 similarly to the first embodiment. Constituent elements having the same functions as those of the first embodiment will be denoted by the same reference numerals as the first embodiment, and redundant description thereof will not be repeated. The difference from the first embodiment will be described below.

In the present embodiment, a flexible material (for example, a methacrylic resin, a cycloolefin polymer resin, and the like) such as resin is used as the substrate 13. A chip having excellent bending resistance can be obtained when a flexible material (for example, a transparent fluoride resin, a silicon resin, an acryl resin, and the like) such as a resin is used for the optical waveguide layer 1 and the protective layer 6. Although in the exemplary configuration of FIG. 6, the reflective film 2 is not provided, a reflective film 2 which is formed of a flexible material (for example, an aluminum deposition film or the like) may be provided between the optical waveguide layer 1 and the substrate 13.

FIGS. 7A to 7G are views showing an example of the method for manufacturing the optical waveguide sensor chip according to the present embodiment. In this example, a case in which the substrate 13, the optical waveguide layer 1, and the protective layer 6 are formed of a flexible resin material, and the reflective film 2 is not provided will be described as an example. In this example, a method in which a chip is formed on a supporting substrate, and then, the chip is separated from the substrate will be described.

Figure 7A:
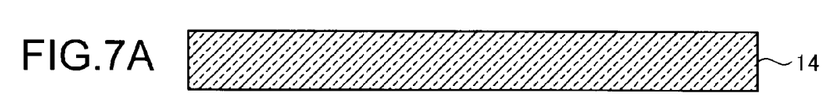
FIGS. 7A to 7G are views of one example of a method for manufacturing the optical waveguide sensor chip according to the third embodiment.

First, as shown in FIG. 7A, a supporting substrate 14 is prepared. Any material may be used as the material of the supporting substrate 14, and glass, a silicon substrate, and the like can be used, for example.

Figure 7B:
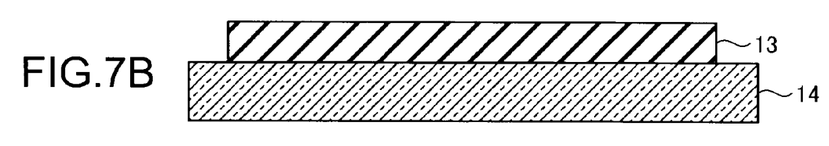
Figure 7C:
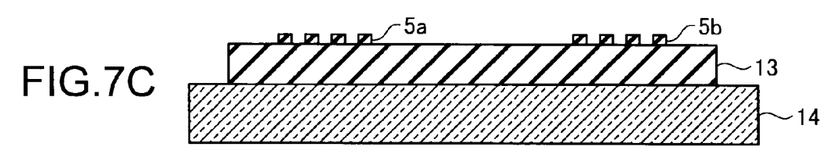

Subsequently, as shown in FIG. 7B, a substrate 13 is formed on the supporting substrate 14. For example, the substrate 13 can be formed by applying a liquid material of the substrate 13 by spin coating and then curing the liquid material. Any curing method may be used, and for example, ultraviolet (UV) irradiation, baking using a hot plate, and the like can be used, for example. Subsequently, as shown in FIG. 7C, gratings 5a and 5b are formed on the substrate 13. The gratings 5a and 5b can be formed by the same method as that used in the first embodiment.

Figure 7D:
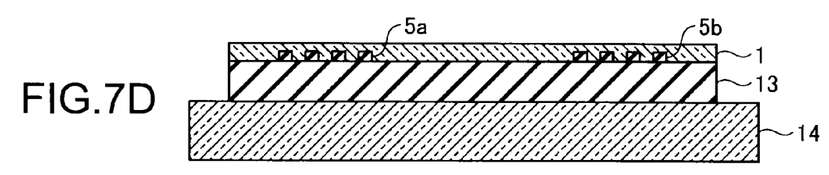
Figure 7E:
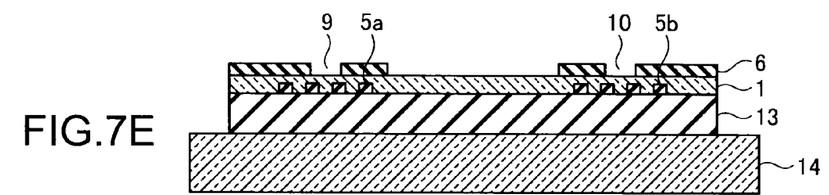
Figure 7F:
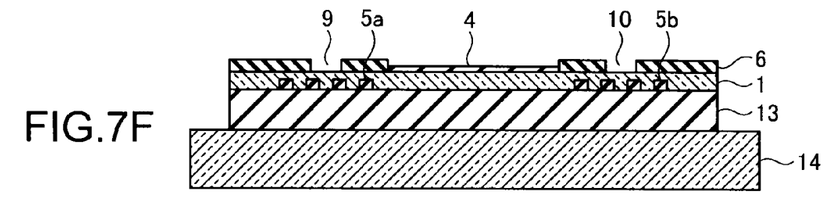

Subsequently, as shown in FIG. 7D, an optical waveguide layer 1 is formed on the substrate 13 and the gratings 5a and 5b. Similarly to the first embodiment, for example, the optical waveguide layer 1 can be formed by applying a liquid material of the optical waveguide layer 1 by spin coating and then curing the liquid material.

Figure 7G:
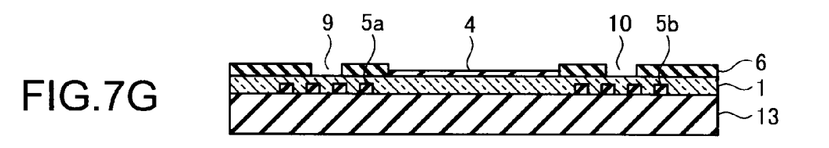

The subsequent processes (FIGS. 7E and 7F) of forming the protective layer 6, the through holes 9 and 10, and the functional film 4 are the same as the processes shown in FIGS. 3E and 3F. After forming the functional film 4, the substrate 13 is separated from the supporting substrate 14, as shown in FIG. 7G.

As described above, in the present embodiment, the substrate 13, the optical waveguide layer 1, and the protective layer 6 are formed of a flexible material. Therefore, it is possible to obtain the same advantageous effects as the first embodiment, and to obtain a chip having excellent bending resistance. Furthermore, it is possible to prevent the occurrence of defective adhesion between the material of the optical waveguide layer and the substrate which can be is observed in the glass substrate.

Fourth Embodiment

FIGS. 8A to 8G are views showing an example of the method for manufacturing an optical waveguide sensor chip according to a fourth embodiment. The optical waveguide sensor chip of the present embodiment has the same configuration as the optical waveguide sensor chip of the first embodiment, except that it includes a rear surface protective layer in place of the substrate 3 of the optical waveguide sensor chip of the first embodiment.

In the present embodiment, a glass substrate is used as the optical waveguide layer 1, thus making the substrate 13 of the second embodiment or the substrate 3 of the first embodiment unnecessary. Instead, on the rear surface of the optical waveguide layer 1, a rear surface protective layer which protects a glass substrate used as the optical waveguide layer 1 from contamination or the like is formed by spin coating, a printing method, or the like, for example.

Figure 8A:
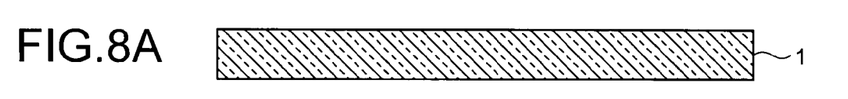
FIGS. 8A to 8G are views of one example of a method for manufacturing an optical waveguide sensor chip according to a fourth embodiment.
Figure 8B:
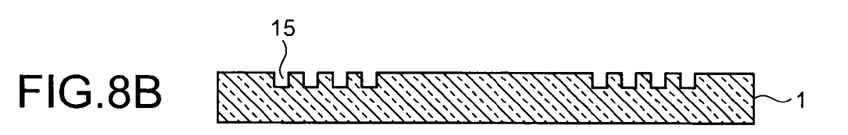

The method for manufacturing the optical waveguide sensor chip according to the fourth embodiment will be described with reference to FIGS. 8A to 8G. First, as shown in FIG. 8A, a glass substrate functioning as the optical waveguide layer 1 is prepared. Then, as shown in FIG. 8B, the optical waveguide layer 1 is etched to form a pattern, whereby grooves 15 are formed. Since the grooves 15 are buried by the material of gratings in a subsequent step to form the gratings 5a and 5b, the grooves 15 are formed based on the shape of the gratings 5a and 5b. The optical waveguide layer 1 may be etched by any method, and wet-etching, RIE, and the like can be used.

Figure 8C:
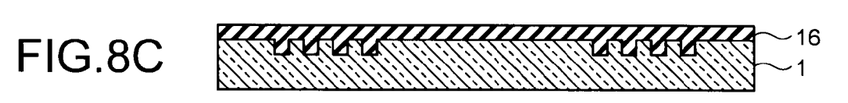

Subsequently, as shown in FIG. 8C, a thin film 16 of the grating material is formed on the optical waveguide layer 1 including the upper portions of the grooves 15 by sputtering, plating, a CVD method, or the like. The material of the thin film 16 is the same as the thin film 5 of the first embodiment.

Figure 8D:
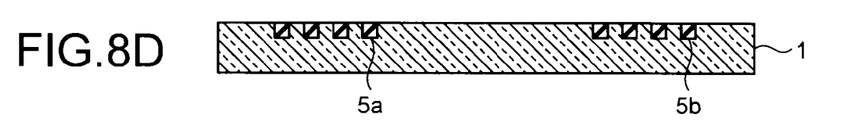

Subsequently, as shown in FIG. 8D, the thin film 16 formed on a planar portion (other than the upper portions of the grooves 15) on the optical waveguide layer 1 is removed, whereby the gratings 5a and 5b are formed. In this case, any method may be used as the method of removing, and polishing can be used, for example.

Figure 8E:
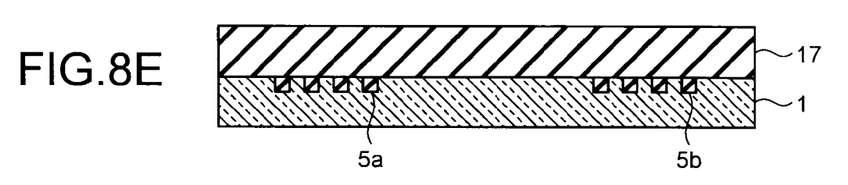

Subsequently, as shown in FIG. 8E, a rear surface protective layer 17 is formed on the rear surface of the optical waveguide layer 1 (the surface on the opposite side of the surface where the gratings 5a and 5b are formed). Any method may be used as the method for forming the rear surface protective layer 17, and spin coating, a printing method, and the like can be used, for example. Moreover, any material may be used as the material of the rear surface protective layer 17, and a fluoride resin, and the like can be used, for example.

Figure 8F:
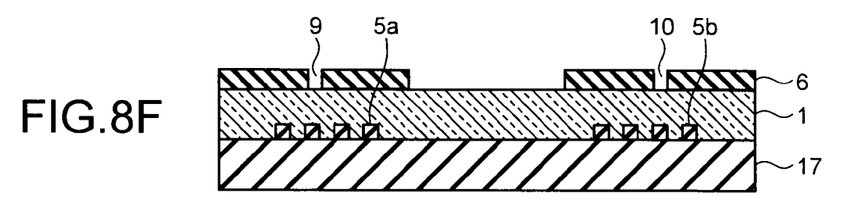
Figure 8G:
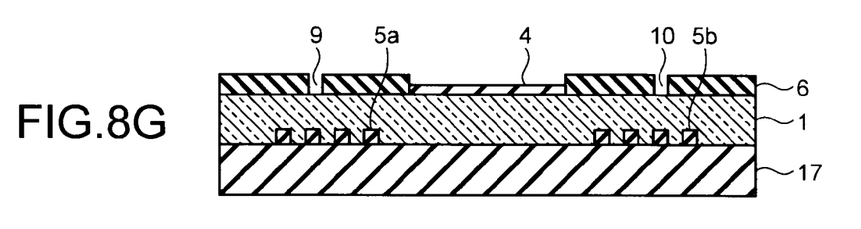

Subsequently, as shown in FIG. 8F, the optical waveguide sensor chip is turned upside down, and similarly to FIG. 3E of the first embodiment, a protective layer 6 is formed on a region of the optical waveguide layer 1, excluding a predetermined region where the functional film 4 is formed and the through holes 9 and 10. After that, as shown in FIG. 8G, the functional film 4 is formed similarly to FIG. 3F of the first embodiment. Although in this example, a case where the reflective film 2 is not provided has been described, the reflective film 2 may be formed before forming the rear surface protective layer 17.

As described above, when a glass substrate is used as the optical waveguide layer 1, the optical waveguide layer 1 becomes thicker (for example, about 100 μm) than that of the first embodiment and the like. When the optical waveguide layer 1 is made further thinner, the processes of FIGS. 8A to 8E may be performed with the thinned glass substrate fixed to a supporting substrate, and the processes subsequent to FIG. 8F may be performed with the glass substrate separated from the supporting substrate.

FIGS. 9A to 9G are views showing another example of the method for manufacturing the optical waveguide sensor chip according to the fourth embodiment. In FIGS. 8A to 8G, an example in which the grooves 15 are formed on the optical waveguide layer 1 to form the gratings 5a and 5b has been described. However, the gratings 5a and 5b may be formed without forming the grooves 15 as shown in FIGS. 9A to 9G.

Figure 9A:
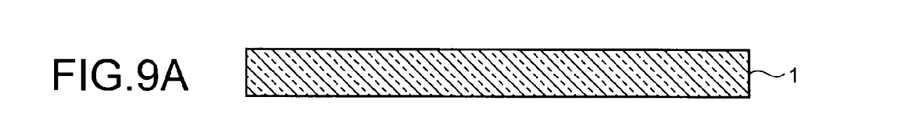
FIGS. 9A to 9G are views of another example of the method for manufacturing the optical waveguide sensor chip according to the fourth embodiment.
Figure 9B:
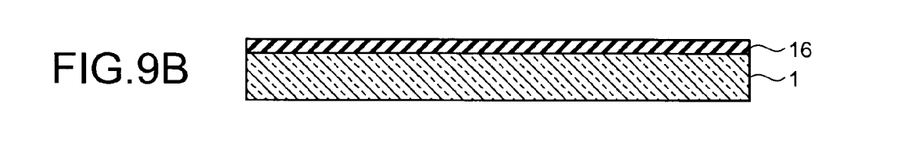
Figure 9C:
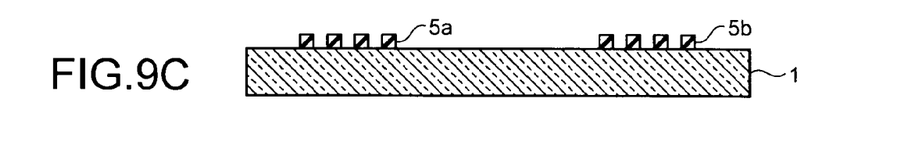

First, as shown in FIG. 9A, a glass substrate functioning as the optical waveguide layer 1 is prepared. Then, as shown in FIG. 9B, a thin film 16 of the grating material is formed on the optical waveguide layer 1 by sputtering, plating, a CVD method, or the like. Subsequently, as shown in FIG. 9C, the thin film 16 is etched to form a pattern, whereby the gratings 5a and 5b are formed at two locations of the entrance side and the exit side. Although the thin film 16 may be etched by any method, RIE can be used, for example.

Figures 9D, 9E:
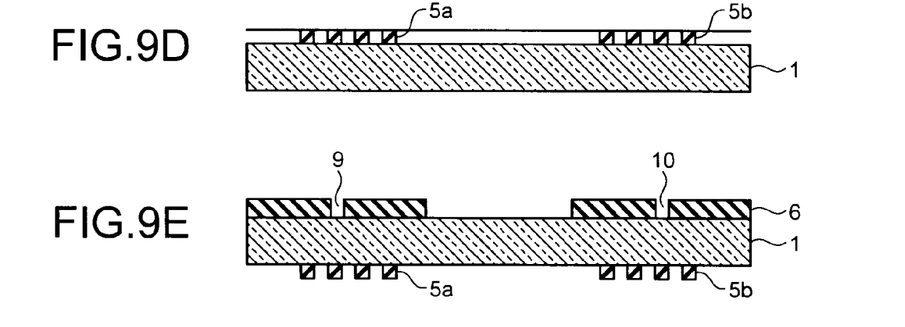

Subsequently, as shown in FIG. 9D, after the gratings 5a and 5b are polished from the upper side, a protective layer 6 is formed on a region of the optical waveguide layer 1 excluding a predetermined region where the functional film 4 is formed and the through holes 9 and 10 as shown in FIG. 9E.

Figure 9F:
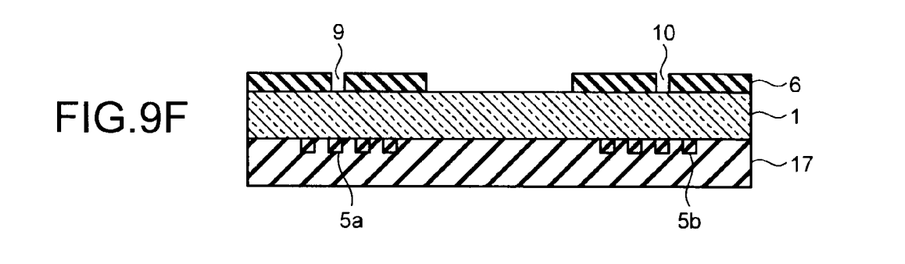
Figure 9G:
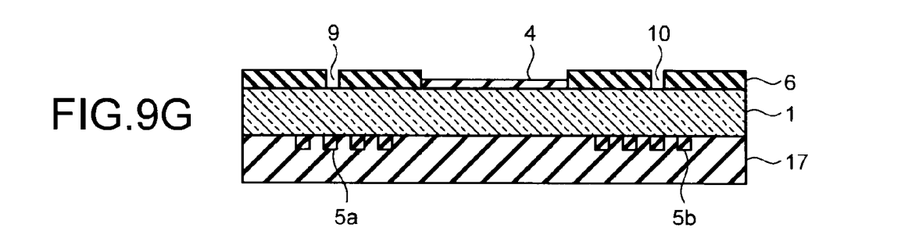

Subsequently, as shown in FIG. 9F, a rear surface protective layer 17 is formed on the rear surface side, and then, the functional film 4 is formed as shown in FIG. 9G.

As described above, in the present embodiment, a glass substrate is used as the optical waveguide layer 1, and the through holes 9 and 10 are formed in an optical waveguide sensor chip having no additional substrate, whereby the light from the light source 7 enters the optical waveguide layer 1 through the through hole 9, and the light exiting from the optical waveguide layer 1 enters the light receiving element 8 through the through hole 10. Therefore, it is not necessary to perform optical design taking the refractive indices of a plurality of materials into account, and light does not lose its power.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An optical waveguide sensor chip comprising:
    an optical waveguide layer;
    a pair of optical elements disposed at both ends of one of the boundary surfaces of the optical waveguide layer so that light enters the optical waveguide layer and the light exits from the optical waveguide layer;
    a functional film formed on a predetermined region of the optical waveguide layer;
    a covering layer formed in a planar region on the light entrance surface of the optical waveguide layer including a planar region where at least the optical elements are disposed;
    a first through hole formed on the covering layer so as to allow the light entering the entrance-side optical element to pass therethrough; and
    a second through hole formed on the covering layer so as to allow the light exiting from the exit-side optical element to pass therethrough.

2. The optical waveguide sensor chip according to claim 1, wherein the covering layer is a surface protective layer which is formed on a region of a surface of the optical waveguide layer where the functional film is formed, excluding the predetermined region.

3. The optical waveguide sensor chip according to claim 1, wherein the covering layer is a substrate which is formed on a rear surface of the surface of the optical waveguide layer where the functional film is formed.

4. The optical waveguide sensor chip according to claim 2, further comprising:

a reflective film formed on a rear surface of a surface of the optical waveguide layer where the functional film is formed; and a non-transparent substrate formed on the reflective film.

5. The optical waveguide sensor chip according to claim 4, wherein the reflective film is a metal thin film.

6. The optical waveguide sensor chip according to claim 3, further comprising:

a reflective film formed on a rear surface of a surface of the optical waveguide layer where the functional film is formed; and a third through hole formed on the reflective film so as to allow the light entering the entrance-side optical element to pass therethrough; and a fourth through hole formed on the reflective film so as to allow the light exiting from the exit-side optical element to pass therethrough.

7. The optical waveguide sensor chip according to claim 3, wherein the substrate is a non-transparent substrate.

8. The optical waveguide sensor chip according to claim 7, wherein the substrate is a silicon substrate.

9. The optical waveguide sensor chip according to claim 3, wherein the covering layer is formed of a resin material.

10. The optical waveguide sensor chip according to claim 1, wherein the optical waveguide layer is formed of a resin material.

11. The optical waveguide sensor chip according to claim 1, wherein the optical waveguide layer is formed of a glass substrate.

12. An optical waveguide sensor comprising:

a light source;

a light receiving element;

an optical waveguide layer;

a pair of optical elements disposed at both ends of one of the boundary surfaces of the optical waveguide layer so that light enters the optical waveguide layer and the light exits from the optical waveguide layer;

a functional film formed on a predetermined region of the optical waveguide layer;

a covering layer formed in a planar region on the light entrance surface of the optical waveguide layer including a planar region where at least the optical elements are disposed;

a first through hole formed on the covering layer so as to allow the light entering the entrance-side optical element to pass therethrough; and a second through hole formed on the covering layer so as to allow the light exiting from the exit-side optical element to pass therethrough.

13. The optical waveguide sensor according to claim 12, wherein the covering layer is a surface protective layer which is formed on a region of a surface of the optical waveguide layer where the functional film is formed, excluding the predetermined region.

14. The optical waveguide sensor according to claim 12, wherein the covering layer is a substrate which is formed on a rear surface of the surface of the optical waveguide layer where the functional film is formed.

15. The optical waveguide sensor according to claim 13, further comprising:

a reflective film formed on a rear surface of a surface of the optical waveguide layer where the functional film is formed; and a non-transparent substrate formed on the reflective film.

16. The optical waveguide sensor according to claim 15, wherein the reflective film is a metal thin film.

17. The optical waveguide sensor according to claim 14, further comprising:

a reflective film formed on a rear surface of a surface of the optical waveguide layer where the functional film is formed; and a third through hole formed on the reflective film so as to allow the light entering the entrance-side optical element to pass therethrough; and a fourth through hole formed on the reflective film so as to allow the light exiting from the exit-side optical element to pass therethrough.

18. The optical waveguide sensor according to claim 14, wherein the substrate is a non-transparent substrate.

* * * * *